(12) United States Patent
Fujimori et al.

(10) Patent No.: US 8,602,977 B2
(45) Date of Patent: Dec. 10, 2013

(54) CAPSULE-TYPE MEDICAL APPARATUS

(75) Inventors: Noriyuki Fujimori, Nagano (JP); Hiroshi Suzushtma, Nagano (JP)

(73) Assignee: Olympus Corporation, Tokyo (JP)

( * ) Notice: Subject to any disclaimer, the term of this patent is extended or adjusted under 35 U.S.C. 154(b) by 1438 days.

(21) Appl. No.: 12/013,883

(22) Filed: Jan. 14, 2008

(65) Prior Publication Data

US 2008/0183041 A1  Jul. 31, 2008

Related U.S. Application Data

(60) Division of application No. 11/487,919, filed on Jul. 17, 2006, now abandoned, which is a continuation of application No. PCT/JP2005/000220, filed on Jan. 12, 2005.

(30) Foreign Application Priority Data

Oct. 27, 2003 (JP) .................... 2003-365570
Jan. 16, 2004 (JP) .................... 2004-009273

(51) Int. Cl.
*A61B 1/06* (2006.01)
(52) U.S. Cl.
USPC ........................................ 600/160
(58) Field of Classification Search
USPC .................... 600/109, 160, 178, 180
See application file for complete search history.

(56) References Cited

U.S. PATENT DOCUMENTS

| 4,844,076 | A | 7/1989 | Lesho et al. |
| 5,414,405 | A | 5/1995 | Hogg et al. |
| 7,295,226 | B1 | 11/2007 | Meron et al. |
| 2001/0035902 | A1 | 11/2001 | Iddan et al. |
| 2003/0095174 | A1 | 5/2003 | Terasaki et al. |
| 2003/0181788 | A1 | 9/2003 | Yokoi et al. |
| 2004/0027459 | A1* | 2/2004 | Segawa et al. ........... 348/207.99 |
| 2004/0171914 | A1* | 9/2004 | Avni .............................. 600/160 |

FOREIGN PATENT DOCUMENTS

| JP | 4-30535 | 3/1992 |
| JP | 2003-275170 | 9/1992 |
| JP | 2001-91860 | 4/2001 |
| WO | WO 01/35813 A1 | 5/2001 |

* cited by examiner

*Primary Examiner* — Philip R Smith
(74) *Attorney, Agent, or Firm* — Scully, Scott, Murphy & Presser, P.C.

(57) ABSTRACT

A capsule-type medical apparatus includes a capsule-shape sealed container accommodating an electric component for executing a predetermined function; and a switch unit arranged in a substantially center of the sealed container, and controlling supply of electric power for driving the electric component according to action of a magnetic field from outside of the sealed container.

5 Claims, 14 Drawing Sheets

CAPSULE-TYPE MEDICAL APPARATUS

CROSS-REFERENCE TO RELATED APPLICATIONS

This application is a divisional application of application of U.S. application Ser. No. 11/487,919 filed on Jul. 17, 2006, which is a continuation of PCT international application Ser. No. PCT/JP2005/000220 filed Jan. 12, 2005 which designates the United States, and which claims the benefit of priority from Japanese Patent Application No. 2004-009273, filed Jan. 16, 2004, each of which are incorporated herein by their reference.

BACKGROUND OF THE INVENTION

1. Field of the Invention

The present invention relates to a capsule-type medical apparatus which is introduced into a subject to collect information inside the subject, particularly to a capsule endoscope.

2. Description of the Related Art

Conventionally, there is known a capsule-type medical apparatus (swallowing type endoscope for medical use) which can take images of alimentary systems such as the stomach to collect the information on the inside of the body cavity by introducing the capsule-type medical apparatus from a mouth into a body cavity. The conventional capsule-type medical apparatus provided as a container which accommodates internal components is stored in a package. A permanent magnet is placed in the package, and the container is arranged close to the permanent magnet by accommodating the container in the package. As a result, the capsule-type medical apparatus becomes a halt state in which all electric power supply to the electrical elements in the container are suppressed by a magnetic field of the permanent magnet. When the container is taken out from the package to separate the container away from the permanent magnet, the influence of the magnetic field of the permanent magnet is released to supply the electric power to the electrical elements in the container (for example, see International Publication WO 01/35813).

In the conventional capsule-type medical apparatus, an illumination unit (light-emitting diode) and an objective lens are fixed in a front portion, and a main block to which a circuit board is fixed and an exterior cover in which the main block is accommodated are located in a rear portion. An image sensor, an image sensor control electric component, a transmission electric component, a power switch, and the like are mounted on a circuit board, and an antenna board is connected to the circuit board. A battery is incorporated into the circuit board. The exterior cover includes a hemispherical transparent cover and a cylindrical cover. The front portion of the main block is covered with the hemispherical transparent cover, and the rear portion of the main block is covered with the cylindrical cover. A rear-end portion of the cylindrical cover is formed in a hemispherical shape. The circuit board is fixed to the main block, the main block is accommodated in the exterior cover, and the transparent cover and the cylindrical cover are bonded in a watertight manner to assemble the capsule-type medical apparatus (for example, see JP-A No. 2001-91860 (KOKAI)).

SUMMARY OF THE INVENTION

A capsule-type medical apparatus according to one aspect of the present invention includes a capsule-shape sealed container accommodating an electric component for executing a predetermined function; and a switch unit arranged in a substantially center of the sealed container, and controlling supply of electric power for driving the electric component according to action of a magnetic field from outside of the sealed container.

A capsule-type medical apparatus according to another aspect of the present invention includes a capsule-shape sealed container having a center axis and an outline of the sealed container formed in a rotational symmetry shape with respect to the center axis, the sealed container being introduced into a subject while accommodating an internal component for executing a predetermined function; and an orientation recognizing unit indicating an accommodation direction about the center axis of the internal component with respect to the sealed container.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a capsule type medical apparatus according to the present invention will be described in detail below with reference to the accompanying drawings. The present invention is not limited to the embodiments. In the following embodiments, a capsule endoscope which is introduced from a mouth of a human or an animal as being the subject into the body cavity to take the image inside the body cavity will be described as an example of the capsule type medical apparatus. The present invention can obviously be applied to not only the capsule endoscope but also various capsule type medical apparatuses including a pH sensor or a temperature sensor.

Figure 1:
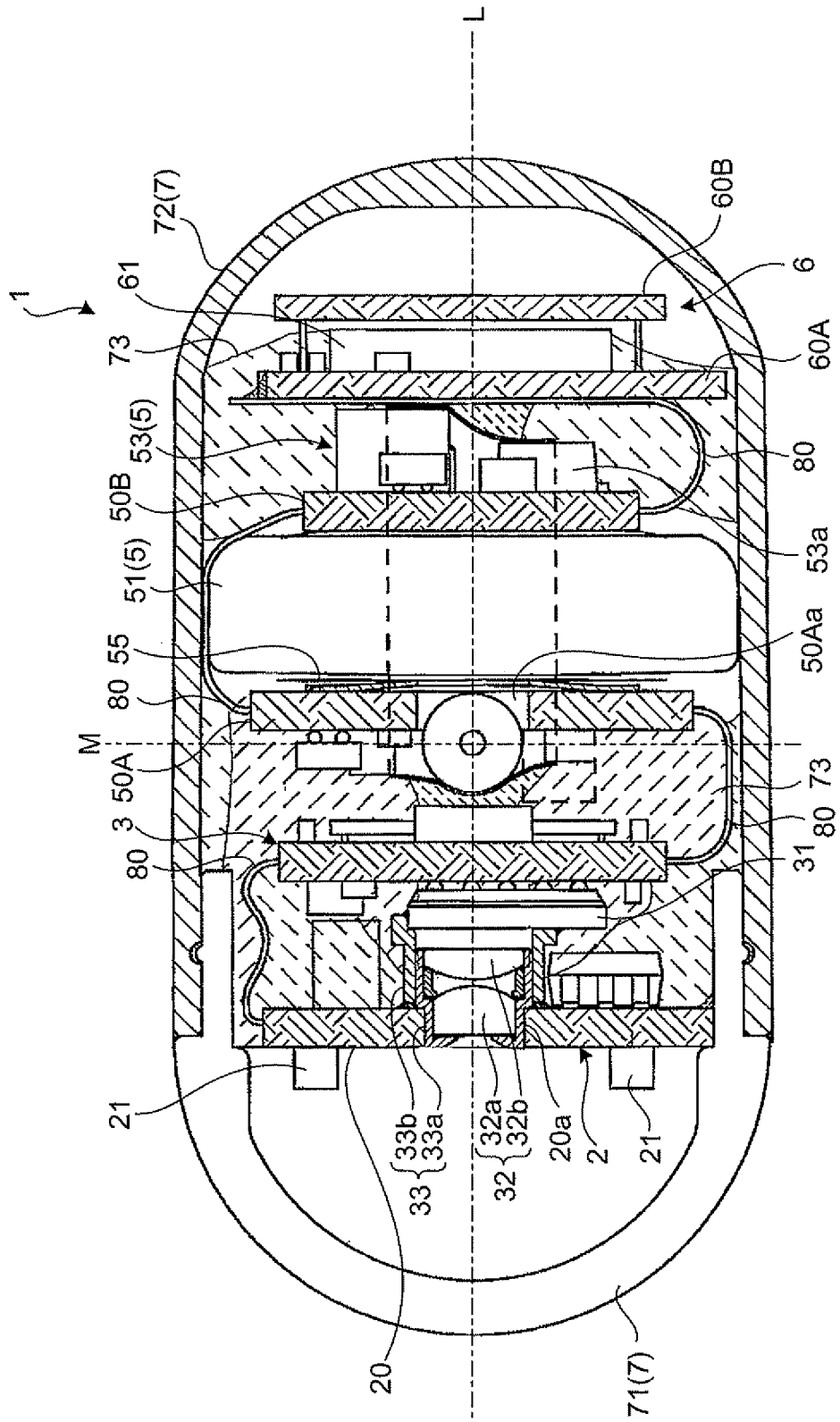
FIG. 1 is a cross-sectional side view showing a configuration of a capsule endoscope as being a capsule-type medical apparatus according to a first embodiment of the invention.

As shown in FIG. 1, a capsule endoscope 1 includes internal components consisting of electronic components, which mainly include an illumination unit 2, an imaging unit 3, a drive unit 4, a power supply unit 5, and a transmission unit 6; and a sealed container 7 accommodating the internal components.

Figure 2:
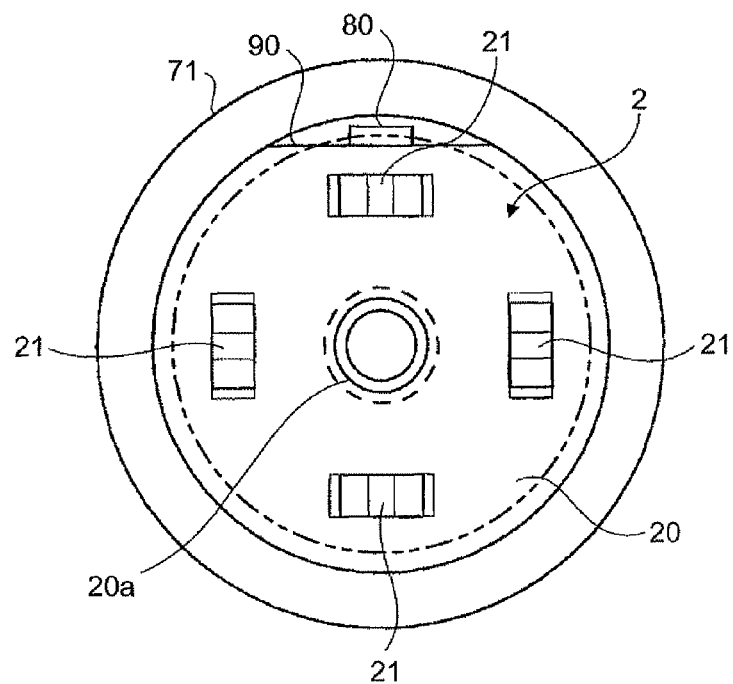
FIG. 2 is a cross-sectional view showing an illumination board when viewed from a front surface.
Figure 3:
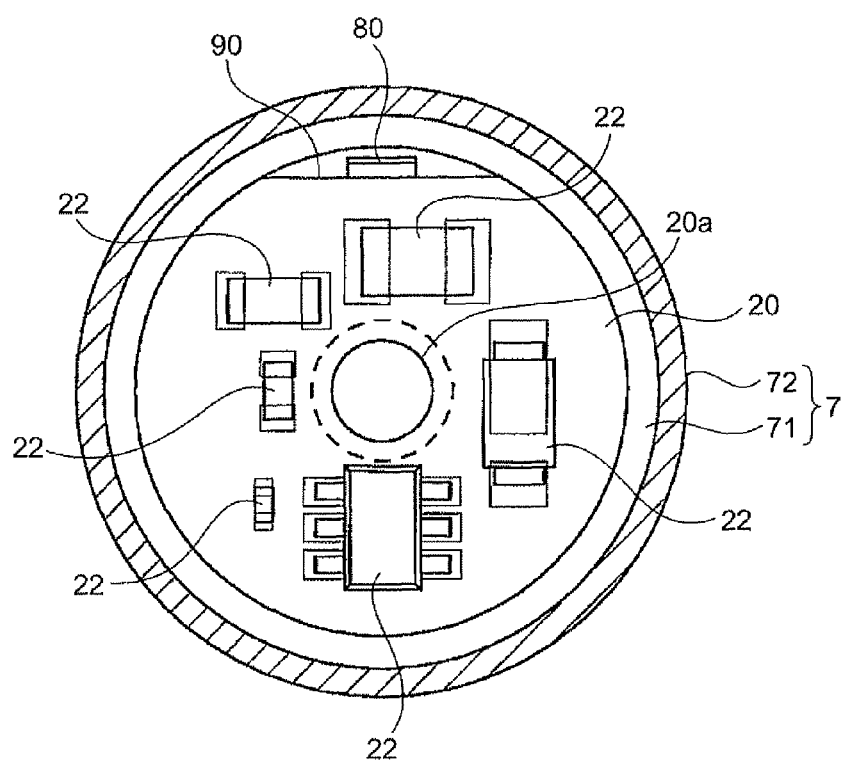
FIG. 3 is a cross-sectional view showing the illumination board when viewed from a back surface.

As shown in FIG. 1, the illumination unit 2 includes an illumination means 21 consisting of an emitter such as a light-emitting diode (for example, white light LED). As shown in FIG. 2, the illumination means 21 are provided on the front surface of a disk-shaped illumination board 20. The illumination board 20 has a through hole 20a at its central portion. Four illumination means 21 are arranged on the left, right, top and bottom of the front surface of the disk-shaped illumination board 20, respectively, with respect to the central through hole 20a. The illumination means 21 emits the illumination light in the forward direction of the illumination board 20. As shown in FIG. 3, chip components 22 which constitute a circuit for driving the illumination means 21 are provided in the back surface of the illumination board 20. The illumination means 21 and the chip components 22 for driving the illumination means 21 are collectively provided in the front surface and back surface of the illumination board 20. This allows downsizing of the illumination board 20 as well as stable operation of the illumination unit 2. The illumination means 21 is not limited to the light-emitting diode, may consist of, for example, an EL device. The number of illumination means 21 is not limited to four.

Figure 4:
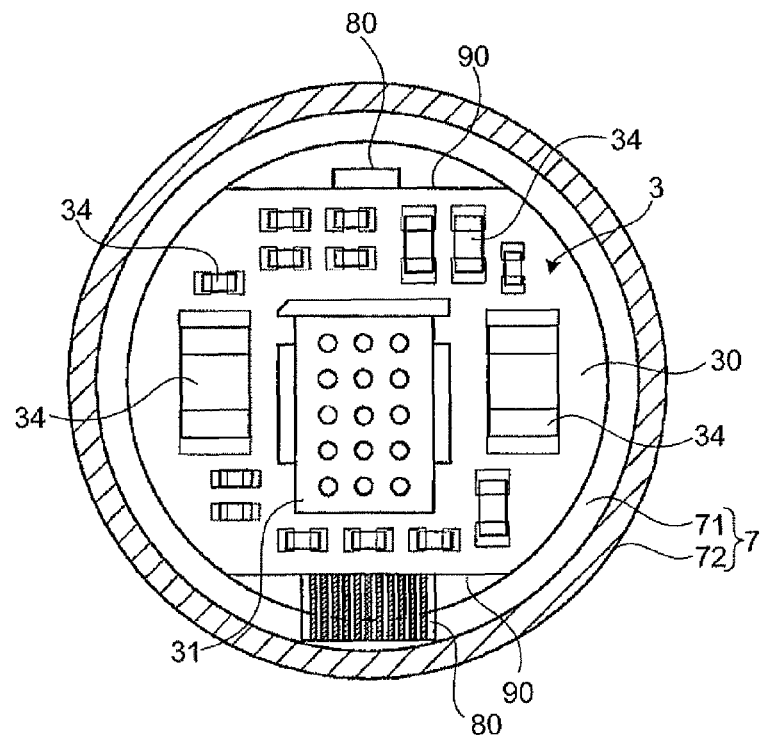
FIG. 4 is a cross-sectional view showing an imaging board when viewed from the front surface.

As shown in FIG. 1, the imaging unit 3 includes a solid-state imaging device 31 such as CCD; and an image lens 32 imaging a subject onto the solid-state imaging device 31. As shown in FIG. 4, the solid-state imaging device 31 is provided on the front surface of the disk-shaped imaging board 30. The image lens 32 is provided in front of the solid-state imaging device 31. Therefore, the solid-state imaging device 31 takes an optical image imaged on its light-acceptance surface through the image lens 32.

As shown in FIG. 1, the image lens 32 consists of a pair of lenses 32a and 32b arranged on the optical axis line of the solid-state imaging device 31. The lenses 32a and 32b are held by a cylindrical lens frame 33a with their optical axes being concentric.

On the other hand, a cylindrical hold frame 33b is provided in front of the solid-state imaging device 31. The hold frame 33b is positioned and fixed with respect to the optical axis line (located on the same straight line as a later-mentioned central axis line L and being a center line of an imaging area of the light-acceptance surface) of the solid-state imaging device 31 optical axis line. The lens frame 33a is movably inserted into and held by the hold frame 33b in a direction along the optical axis with respect to the hold frame 33b. That is, the lens frame 33a and the hold frame 33b constitute a focus adjustment mechanism 33 which moves the image lens 32 along the optical axis. The focus adjustment mechanism 33 can absorb production variations in lens frame 33a and image lens 32 to set desired resolution, depth of field, and view angle. The lens frame 33a is inserted into the through hole 20a of the illumination board 20, and the optical axis of the image lens 32 is orientated toward the front surface of the illumination board 20. Accordingly, the imaging unit 3 can image a range illuminated with the illumination light of the illumination unit 2.

Figure 5:
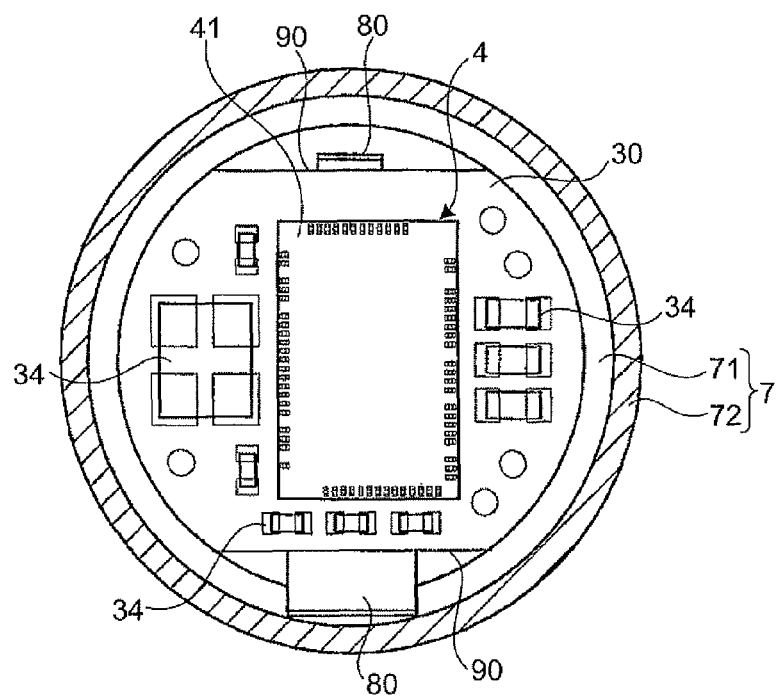
FIG. 5 is a cross-sectional view showing the imaging board when viewed from the back surface.

Since the optical axis of the imaging unit 3 is substantially orthogonal to the illumination board 20, a light distribution of an observation image can be secured when the subject is illuminated with the illumination light emitted from the illumination means 21, and the downsizing of the capsule endoscope 1 including the illumination unit 2 and the imaging unit 3 can be achieved. As shown in FIGS. 4 and 5, chip components 34 which constitute the circuit for driving the solid-state imaging device 31 are provided on the front surface and the back surface of the imaging board 30 while surrounding the solid-state imaging device 31. The solid-state imaging device 31 consists of not only CCD but also CMOS, for example.

The drive unit 4 includes a DSP 41 (Digital Signal Processor). As shown in FIG. 5, the DSP 41 is provided on the back surface of the imaging board 30 while surrounded by the chip components 34. The DSP 41 plays a main role of drive control of the capsule endoscope 1 of the first embodiment and performs the drive control of the solid-state imaging device 31, output signal processing of the solid-state imaging device 31, and the drive control of the illumination means 21.

A semiconductor component can be cited as an example of the chip component 34 provided on the back surface of the imaging board 30. For example, the semiconductor component has a function of mixing an image signal and a clock signal into one signal when the image signal and clock signal outputted from the DSP 41 are transmitted.

As shown in FIG. 1, the power supply unit 5 includes a battery 51, a switch unit 52, and a power supply unit 53. The battery 51 is, for example, a button-shaped silver oxide battery whose outline is round and is arranged so that its negative electrode is located toward the rear side. The battery 51 consists of not only the silver oxide battery but also a rechargeable type battery, a generating type battery, for example.

Figure 6:
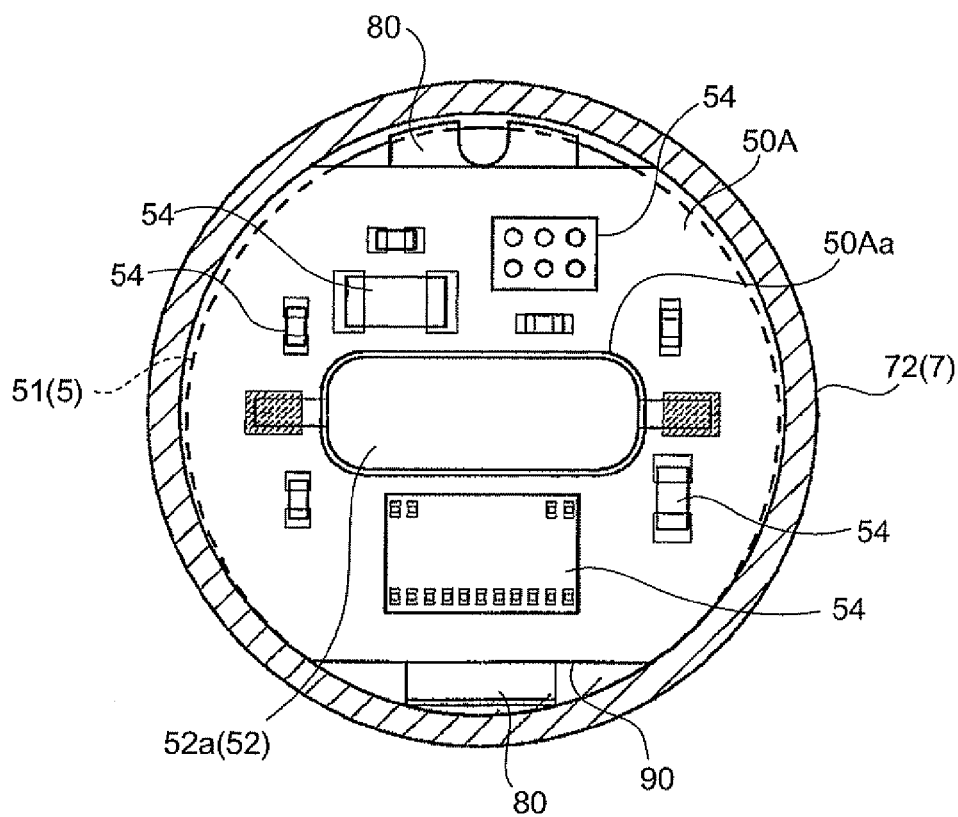
FIG. 6 is a cross-sectional view showing a switch board when viewed from the front surface.
Figure 7A:
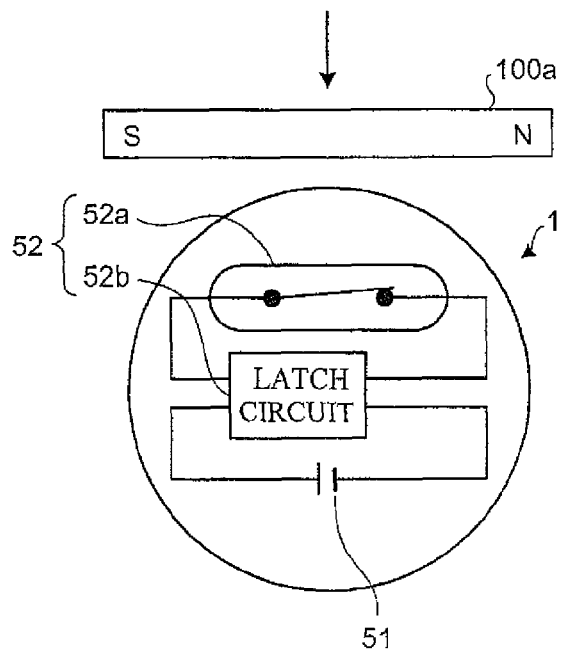
FIGS. 7A and 7B are schematic views showing a switch unit.
Figure 7B:
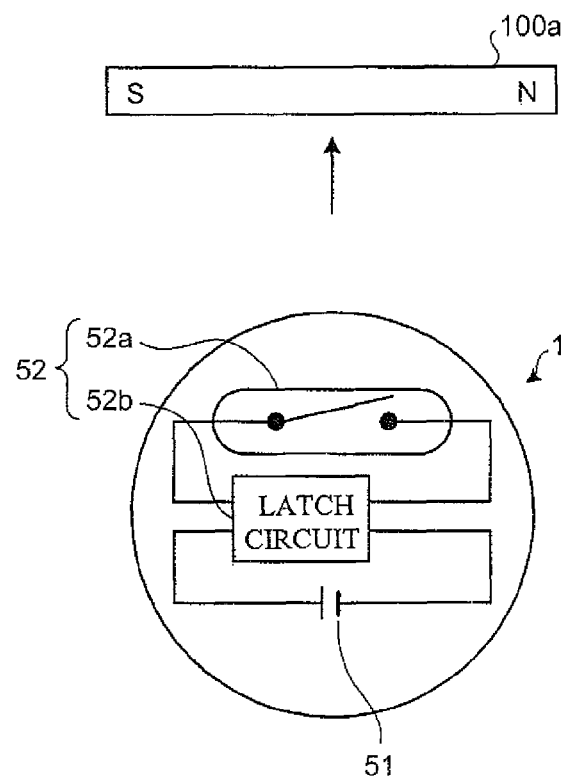

As shown in FIG. 1, the switch unit 52 includes a reed switch 52a as being a switch means; and a latch circuit 52b (shown in FIGS. 7A and 7B). As shown in FIG. 6, the reed switch 52a is provided on the front surface of a disk-shaped switch board 50A. As shown in FIG. 1, the reed switch 52a is inserted into a cutout hole 50Aa made in the switch board 50A and is fixed by an adhesive agent, so that a projection height of the reed switch 52a toward the front surface of the switch board 50A is suppressed to achieve the downsizing of the switch board 50A. The reed switch 52a is a normally-OFF type switch. As shown in FIG. 7A, a pair of reed relays internally provided come into contact with each other to become an ON state by bringing the magnetic field (permanent magnet and the like) close to the reed relays from the outside. On the other hand, as shown in FIG. 7B, the reed relays are separated from each other to become an OFF state by separating the magnetic field away from the reed relays. The latch circuit 52b holds the OFF state of a main power supply of the capsule endoscope 1 when the reed switch 52a becomes the ON state; the latch circuit 52b holds the ON state of the main power supply of the capsule endoscope 1 when the reed switch 52a becomes the OFF state. That is, in the switch unit 52, the reed switch 52a becomes the ON state by bringing the magnetic field (permanent magnet 100a) close to the reed switch 52a, which causes the latch circuit 52b to hold the OFF state of the main power supply of the capsule endoscope 1. On the other hand, in the switch unit 52, the reed switch 52a becomes the OFF state by separating the magnetic field (permanent magnet 100a) from the reed switch 52a, which causes the latch circuit 52b to hold the ON state of the main power supply of the capsule endoscope 1.

As shown in FIG. 6, chip components 54 are provided in the front surface of the switch board 50A. The chip components 54 constitute the latch circuit 52b. Examples of the chip component 54 include a memory and an oscillator. For example, an initial value of the DSP 41, variations in color or white balance of the solid-state imaging device 31, and a specific number of the capsule endoscope 1 are stored in the memory. The oscillator supplied a basic clock to the DSP 41. As shown in FIG. 1, a contact 55 formed from a leaf spring is provided in the back surface of the switch board 50A. The contact 55 is in contact with a positive electrode of the battery 51.

Figure 8:
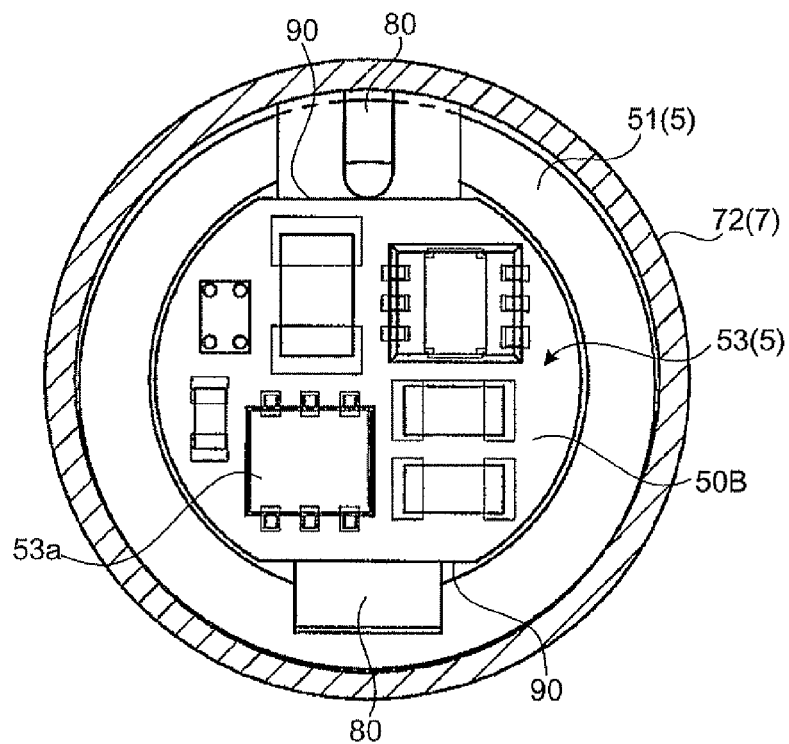
FIG. 8 is a cross-sectional view showing a power supply board when viewed from the back surface.

The power supply unit 53 includes a DC-DC converter 53a. As shown in FIG. 8, the DC-DC converter 53a is provided in a back surface of a disk-shaped power supply board 50B. The DC-DC converter 53a controls the voltage supplied from the battery 51 in order to always obtain the constant voltage necessary for the system. A contact (not shown), which is in contact with the negative electrode of the battery 51, is provided in the front surface of the power supply board 50B. Thus, in the power supply unit 5, the battery 51 is connected between the switch board 50A and the power supply board 50B to supply the electric power.

Figure 9:
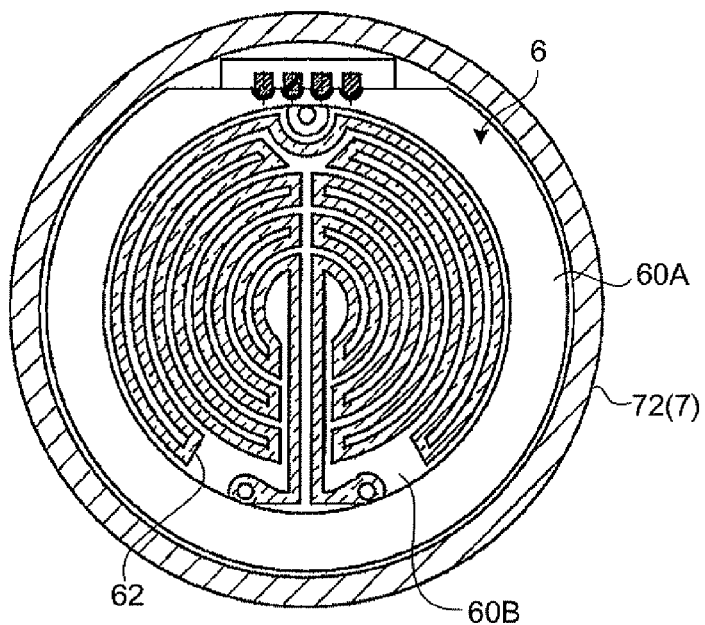
FIG. 9 is a cross-sectional view showing an antenna board when viewed from the back surface.

The transmission unit 6 includes an oscillator circuit 61 and an antenna 62. As shown in FIGS. 1 and 9, the oscillator circuit 61 is provided in the back surface of a disk-shaped transmission board 60A. As shown in FIG. 9, the antenna 62 is provided in a substantially spiral pattern in the back surface of a disk-shaped antenna board 60B. The transmission unit 6 takes out the signal having constant frequency, amplitude, and waveform from the signals to which the mixing is already performed by the semiconductor component. Then, the transmission unit 6 transmits the taken-out signal to the outside through the antenna 62. The transmission board 60A and the antenna board 60B are electrically connected to integrally form a transmission unit by soldering.

The illumination board 20, the imaging board 30, the switch board 50A, and the power supply board 50B are formed from a rigid board. As shown in FIG. 1, the rigid boards are provided while sandwiching a series of flexible boards 80. The rigid boards are provided through the flexible boards 80 in the order of the illumination board 20, the imaging board 30, the switch board 50A, and the power supply board 50B. The rigid boards are electrically connected to each other. As shown in FIG. 1, the boards 20, 30, 50A, and 50B on which the components are provided are arranged while laminated in the lengthwise direction of the capsule endoscope 1 by folding the flexible boards 80. As shown in FIGS. 2 to 6 and 8, in edge portions of boards 20, 30, 50A, and 50B to which the flexible board 80 are extended, flat portions 90 are formed to suppress deformation of the flexible board 80 when the flexible board 80 is folded. Thus, the boards 20, 30, 50A, and 50B and the flexible boards 80 constitute a rigid and flexible board which is integrally and electrically connected. As shown in FIGS. 1 and 9, the flexible board 80 extended from a lower edge portion of the power supply board 50B is electrically connected to the transmission board 60A constituting the transmission unit.

As shown in FIG. 1, the sealed container 7 accommodates the internal components, and the sealed container 7 includes a front cover 71 and a case 72 which are of an exterior material. The front cover 71 and the case 72 are connected to each other. The front cover 71 is arranged on the front side of the capsule endoscope 1, and the front surface side of the illumination board 20 is covered with the front cover 71. The front cover 71 is formed in a hemispherical and dome shape, and the rear side of the front cover 71 is circularly opened. The front cover 71 has transparency or translucency, and the front cover 71 transmits the image illuminated with the illumination light to the inside of the sealed container 7 while transmitting the illumination light emitted from the light-emitting device 23 to the outside of the sealed container 7. For example, a cycloolefin polymer, polycarbonate, acryl, polysulfone, and urethane can be used as the front cover 71. Particularly, the cycloolefin polymer or polycarbonate can preferably used in securing the optical performance and strength of the front cover 71.

The case 72 is a portion with which the internal components are covered on the rear side of the front cover 71. In the case 72 a cylindrical drum portion and a substantially hemispherical and dome-shape rear-end portion are integrated, and the front side of the drum portion is circularly opened. In the case 72, the drum portion accommodates the illumination board 20 of the illumination unit 2, the imaging board 30 of the imaging unit 3, the switch board 50A and power supply board 50B of the power supply unit 5, and the battery 51, and the dome-shape rear-end portion accommodates the transmission board 60A and antenna board 60B of the transmission unit 6. For example, a cycloolefin polymer, polycarbonate, acryl, polysulfone, and urethane can be used as the case 72. Particularly, polysulfone can preferably used in consideration of the strength of the case 72.

As shown in FIG. 1, openings of the front cover 71 with which the front surface side of the illumination board 20 is covered and the case 72 with which the internal components are covered are bonded to each other with the adhesive agent while the watertightness is secured in the sealed container 7. In order to accommodate the internal components in the sealed container 7, gaps between the sealed container 7 and the illumination board 20, the imaging board 30, and the switch board 50A and gaps between the sealed container 7 and the power supply board 50B, the transmission board 60A, and the antenna board 60B are filled with sealing resin 73 which seal the gaps. In addition, gaps between an inner circumference of the sealed container 7 and outer circumferences of the internal components except for the antenna board 60B are sealed by filling the gaps with the sealing resin 73.

In the capsule endoscope 1 having the above configuration, the outline of the sealed container 7 is formed in a rotational symmetry shape with respect to the lengthwise axis direction, i.e., a central axis line L (shown in FIG. 1) by the substantially hemispherical front cover 71 and the cylindrical drum portion and substantially hemispherical rear-end portion of the case 72. The outline of the sealed container 7 is also molded into a mirror-image symmetry shape with respect to a mirror-image symmetry plane M (shown in FIG. 1) in the lengthwise direction. The shape is a so-called capsule shape, and the capsule shape is preferable shape for passing through the body cavity because the capsule shape has neither corner portion nor projection portion.

In the capsule endoscope 1 including the sealed container 7 having the above described shape, the reed switch 52a of the switch unit 52 is arranged in the substantially center of the symmetrical shape. Specifically, as shown in FIG. 1, in the sealed container 7 formed in the rotational symmetry shape, the reed switch 52a is arranged in the substantially center of the rotational symmetry and at the position on the central axis line L of the rotational symmetry. Further, as shown in FIG. 1, in the sealed container 7 formed in the mirror-image symmetry shape, i.e., in the symmetrical shape with respect to the central axis line L or the predetermined plane M orthogonal to the lengthwise axis, the reed switch 52a is arranged in the substantially center of the mirror image symmetry and at the position on the mirror-image symmetry plane M.

Figure 10:
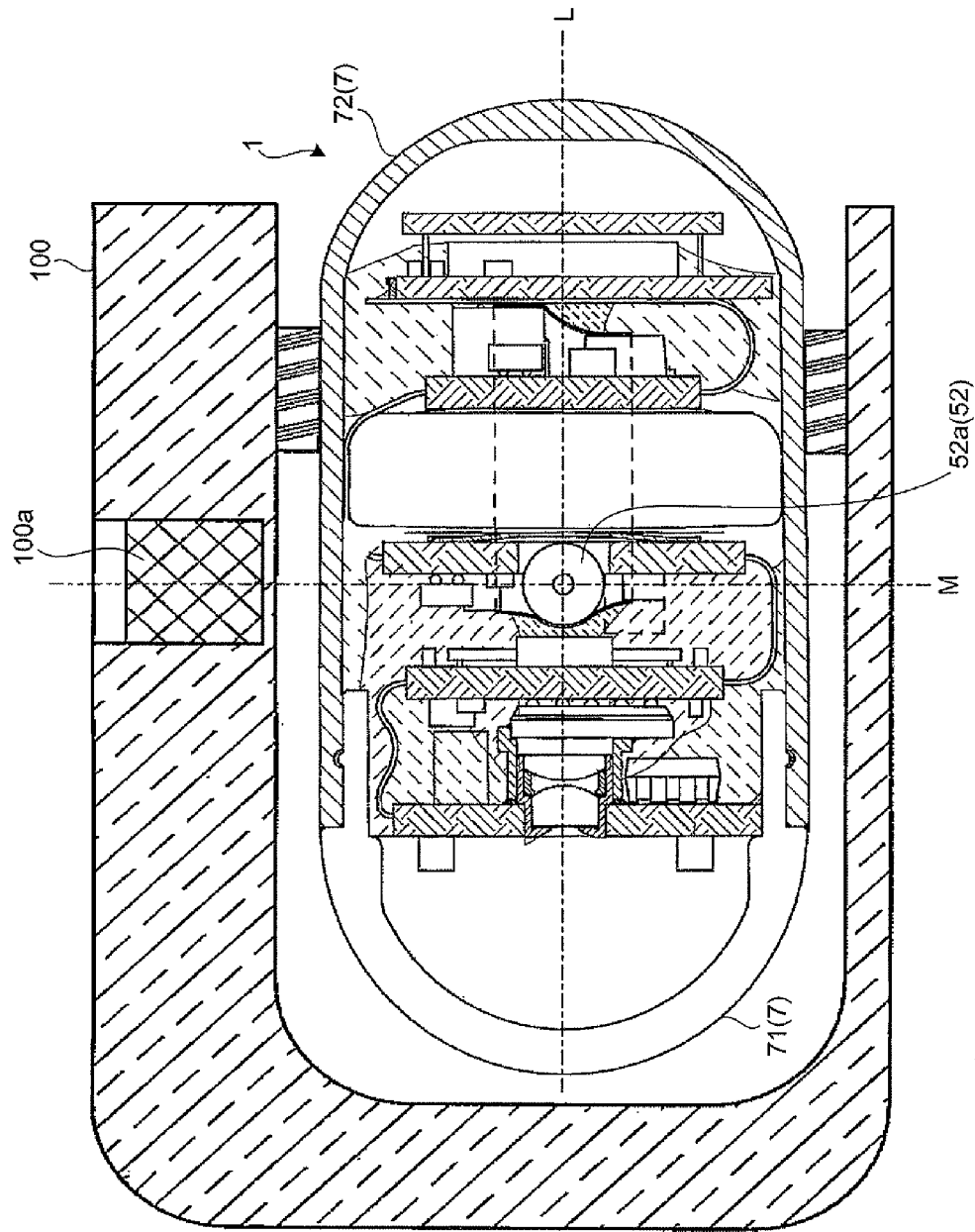
FIG. 10 is a longitudinal sectional view showing a state in which the capsule-type medical apparatus of the invention is accommodated in a package.
Figure 11:
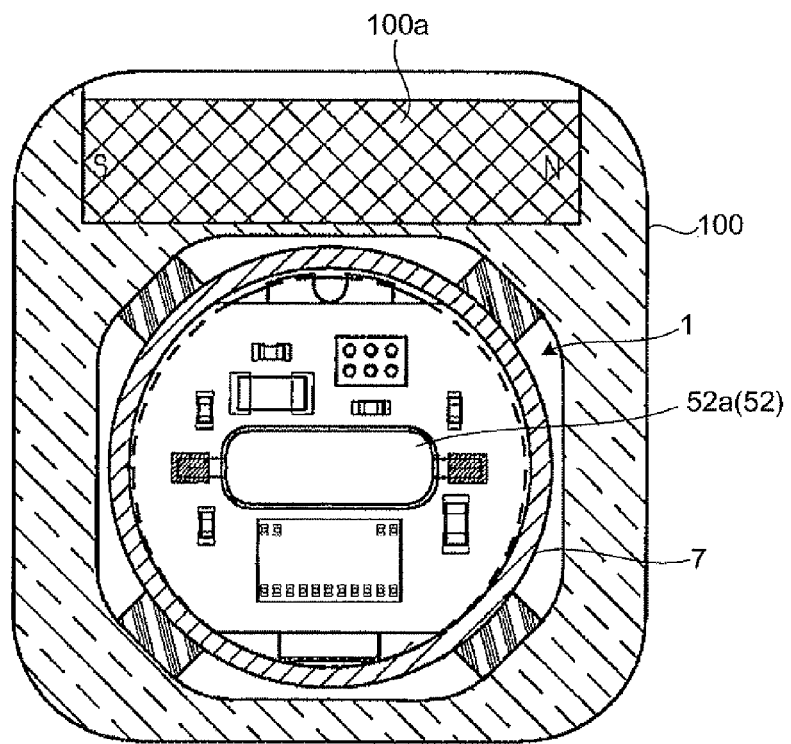
FIG. 11 is a transverse sectional view showing the state in which the capsule-type medical apparatus of the invention is accommodated in the package.

As shown in FIGS. 10 and 11, the capsule endoscope 1 having the above configuration has portability while stored in a package 100. A permanent magnet 100a as being the external magnet is provided in the package 100. When the sealed container 7 is stored in the package 100, the permanent magnet 100a causes the reed switch 52a of the switch unit 52 to turn in the ON-state by the magnetic field. That is, the permanent magnet 100a turns off the power of the capsule endoscope 1. At this point, when the capsule endoscope 1 is stored in the package 100 while the reed relay of the reed switch 52a is orientated in parallel to the lengthwise direction (direction between magnetic poles) of the permanent magnet 100a, the magnetic field acts favorably on the reed switch 52a, so that the reed switch 52a is stably operated.

Figure 12:
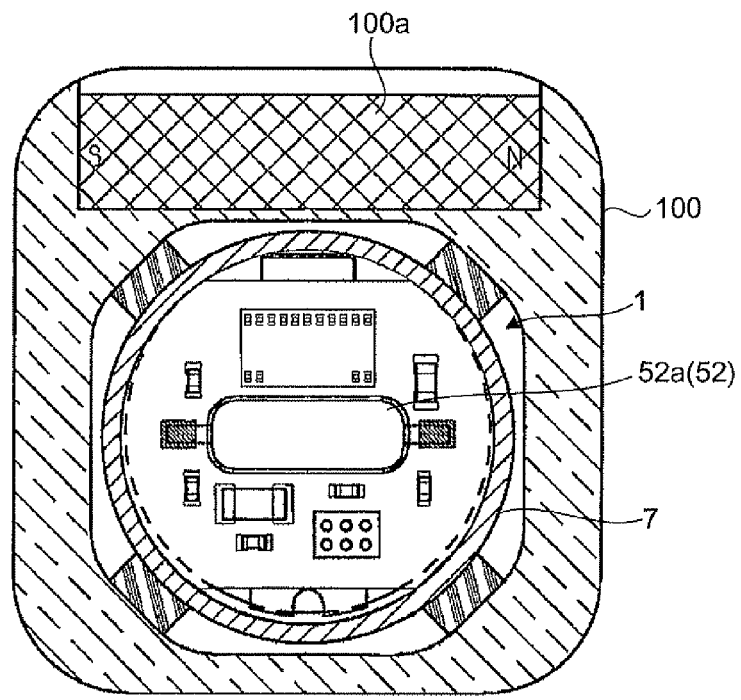
FIG. 12 is a transverse sectional view showing a state in which the capsule-type medical apparatus of the invention is accommodated in the package while rotated in a direction of rotational symmetry.

Thus, when the capsule endoscope 1 is stored in the package 100, the sealed container 7 is formed in the rotationally symmetrical shape. Therefore, even if the capsule endoscope 1 is rotated about the central axis line L, the capsule endoscope 1 can be stored in the package 100. In this case, because the reed switch 52a is arranged at the position on the central axis line L as described above, for example, as shown in FIG. 12, the capsule endoscope 1 which is rotated by 180 degrees with respect to the storage state shown in FIG. 11 is stored in the package 100, the reed switch 52a can be arranged at the position which the magnetic field of the permanent magnet 100a acts on.

Figure 13:
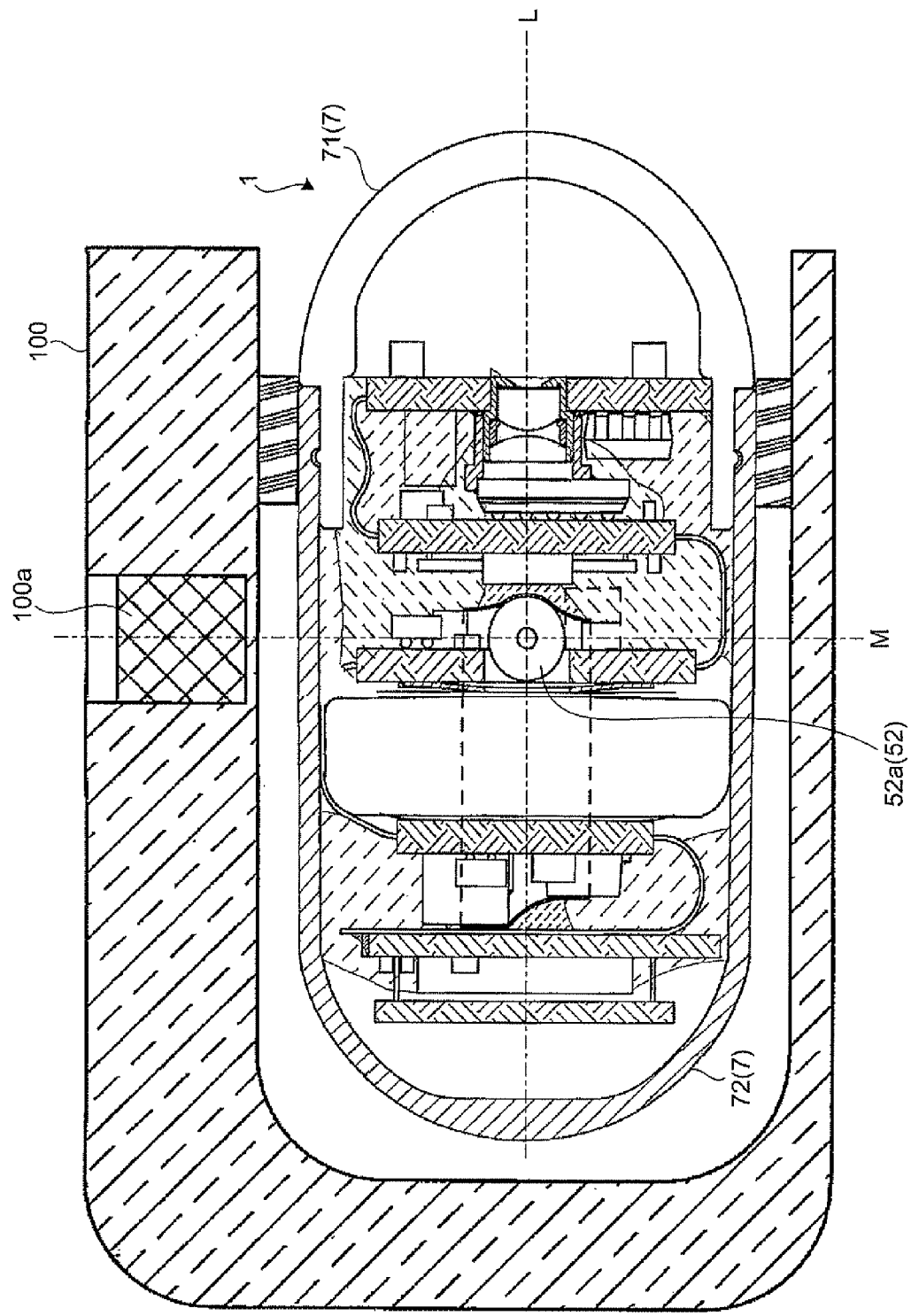
FIG. 13 is a transverse sectional view showing a state in which the capsule-type medical apparatus of the invention is accommodated in the package while reversely rotated in a direction of rotational symmetry.

When the capsule endoscope 1 is stored in the package 100, the sealed container 7 is formed in the mirror-image symmetry shape in the lengthwise direction. Therefore, even if the capsule endoscope 1 is turned around about the mirror-image symmetry plane M, the capsule endoscope 1 can be stored in the package 100. In this case, because the reed switch 52a is arranged at the position of the mirror-image symmetry plane M as described above, for example, as shown in FIG. 13, the capsule endoscope 1 which is turned around in the lengthwise direction about the mirror-image symmetry plane M with respect to the storage state shown in FIG. 10 is stored in the package 100, the reed switch 52a can be arranged at the position which the magnetic field of the permanent magnet 100a acts on.

An example of a medical system in which the capsule endoscope 1 is used will be described below. As shown in FIGS. 10 to 14, the capsule endoscope 1 has the portability while stored in the package 100. As described above, in the capsule endoscope 1 stored in the package 100, the reed switch 52a of the switch unit 52 is turned in the ON state to turn off the main power supply.

The medical system in which the capsule endoscope 1 is used includes the capsule endoscope 1 stored in the package 100, a jacket 102 which a patient, i.e., a subject 101 wears, a receiver 103 which is detachably attached to the jacket 102, and a computer 104.

The jacket 102 is formed in a shielded jacket made of electromagnetic shielding fiber. Antennas 102a to 102d, which pick up radio waves transmitted from the antenna 62 of the capsule endoscope 1, are provided in the capsule endoscope 1, and the capsule endoscope 1 can communicate with the receiver 103 through the antennas 102a to 102d. The number of antennas is not limited to the four antennas 102a to 102d shown in FIG. 14 as long as the plural antennas are used. The radio wave can be well received at the position depending on the movement of the capsule endoscope 1 by selecting the antenna having the strongest received intensity from the antennas 102a to 102d. The position of the capsule endoscope 1 in the body cavity can also be detected from the received intensity of each of the antennas 102a to 102d.

The receiver 103 performs the white balance process to the taken image data sequentially received, and the image data to which the white balance process is already performed is stored in a CompactFlash® memory card (CF memory card) 105. The reception performed by the receiver 103 is not synchronized with imaging start timing of the capsule endoscope 1, but the reception start and the reception end are controlled by operating an input unit of the receiver 103.

The computer 104 reads and writes the CF memory card 105. The computer 104 has a processing function in order that a doctor or a nurse (examiner) makes a diagnosis based on the images of organs in the patient body taken by a doctor or a nurse with using the capsule endoscope 1.

Figure 14:
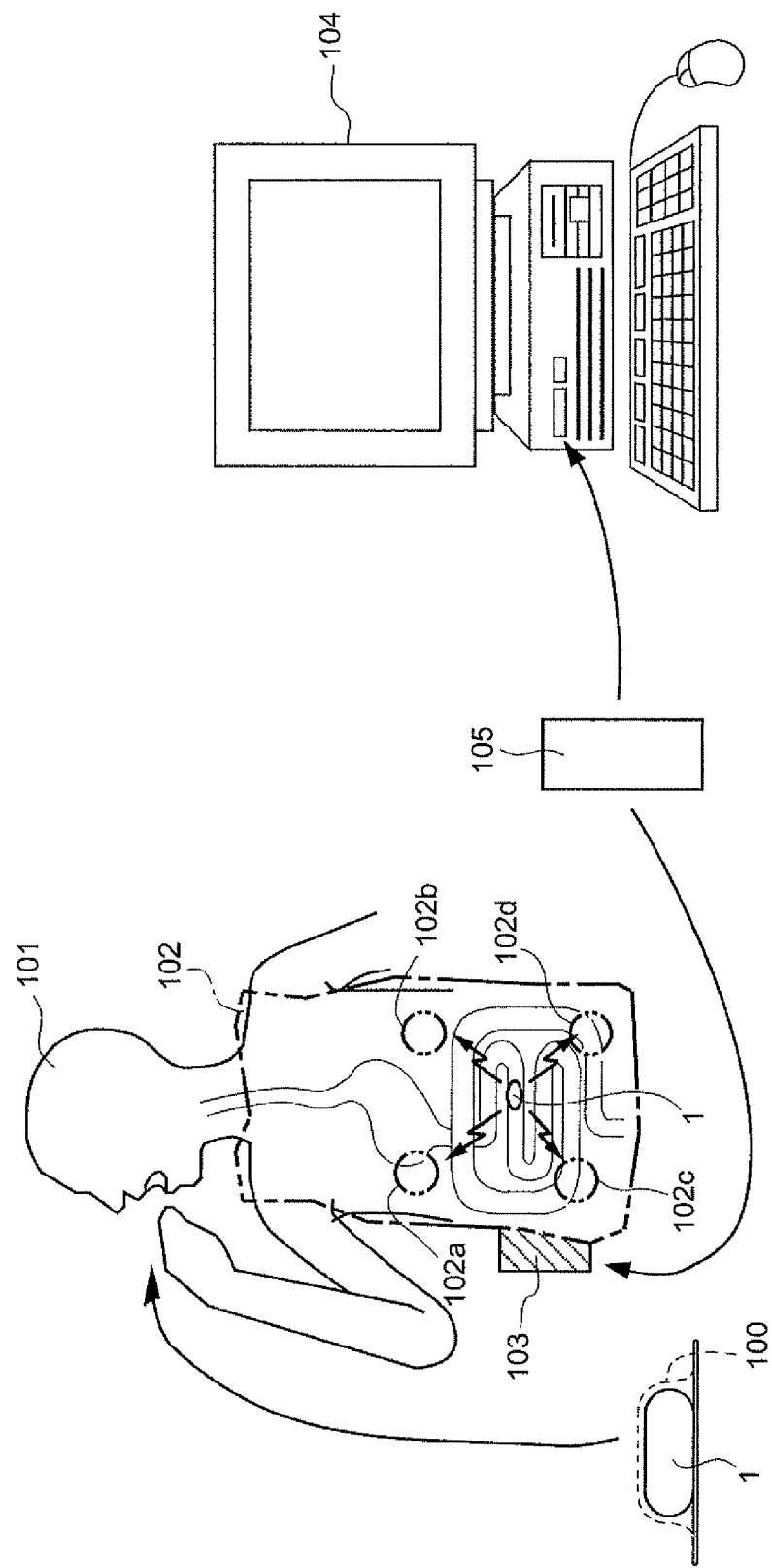
FIG. 14 is a schematic view showing a medical system in which the capsule-type medical apparatus of the invention is used.

The schematic operation of the medical system will be described below. As shown in FIG. 14, before diagnostic examination is started, the capsule endoscope 1 is taken out from the package 100. Therefore, the reed switch 52a of the capsule endoscope 1 becomes the OFF state to turn on the main power supply. That is, the capsule endoscope 1 becomes the state in which the illumination means 21 emits the illumination light to illuminate the outside of the sealed container 7 through the front cover 71, and the capsule endoscope 1 becomes the state in which the image transmitted through the front cover 71 can be images onto the solid-state imaging device 31 in the sealed container 7 to transmit the image data to the outside of the sealed container 7.

The subject 101 swallows the capsule endoscope 1 from the mouth. Then, the capsule endoscope 1 passes through a gullet and progresses through the body cavity by vermicular movements of alimentary canals. Therefore, the capsule endoscope 1 sequentially takes the images in the body cavity while the body cavity is illuminated with the capsule endoscope 1. The capsule endoscope 1 outputs the radio waves of the taken image as needed. The antennas 102a to 102d of the jacket 102 pick up the radio waves. The radio waves picked up by the antennas 102a to 102d is transmitted to the receiver 103 in the form of the signal.

Finally, when the observation (diagnostic examination) of the subject 101 by the capsule endoscope 1 is ended, the CF memory card 105 in which the taken image data is stored is taken out from the receiver 103 and inserted into a memory card insertion hole of the computer 104. In the computer 104, the taken image data stored in the CF memory card 105 is read and stored according to the individual patient.

As described above, in the configuration of the capsule endoscope 1 of the first embodiment, the reed switch 52a is accommodated in the sealed container 7 formed in the rotational symmetry shape, and the reed switch 52a is arranged at the position on the central axis line L of the rotational symmetry. Therefore, even if the sealed container 7 is stored in the package 100 while rotated about the central axis line L, the magnetic field of the permanent magnet 100a provided in the package 100 acts on the reed switch 52a.

In configuration of the capsule endoscope 1 of the first embodiment, the reed switch 52a is accommodated in the sealed container 7 formed in the mirror-image symmetry shape, and the reed switch 52a is arranged at the position of the mirror-image symmetry plane M. Therefore, even if the sealed container 7 is stored in the package 100 while turned around about the mirror-image symmetry plane M, the magnetic field of the permanent magnet 100a provided in the package 100 acts on the reed switch 52a.

Thus, in the capsule endoscope 1 of the first embodiment, the reed switch 52a is arranged in the substantially center of the sealed container 7 formed in the symmetrical shape. Therefore, even if the sealed container 7 is stored in the package 100 while the orientation of the sealed container 7 is changed in the symmetric direction, the magnetic field of the permanent magnet 100a provided in the package 100 acts on the reed switch 52a, so that the reed switch 52a can securely be operated to the external magnetic field.

In the first embodiment, the switch unit 52 includes the reed switch 52a as being the switch unit and the latch circuit 52b which holds the ON and OFF states of the main power supply of the capsule endoscope 1 according to the ON and OFF states of the reed switch 52a. However, the invention is not limited to the configuration of the switch unit of the first embodiment. For example, when the main power supply of the capsule endoscope 1 is turned on by separating the magnetic field away from the switch unit while the main power supply of the capsule endoscope 1 is turned off by bringing the magnetic field close to the switch unit, the latch circuit 52b is not required.

In a second embodiment, the configurations except for the power supply unit 5 and an example of the medical system in which the capsule endoscope 1 is used are similar to those of the first embodiment. Therefore, in the second embodiment, the same components as the first embodiment are designated by the same reference characters, and the descriptions of the configurations of the illumination unit 2, imaging unit 3, drive unit 4, and transmission unit 6 and an example of the medical system in which the capsule endoscope 1 is used will be omitted. Accordingly, in the second embodiment, the power supply unit 5 will be described in detail.

Figure 15:
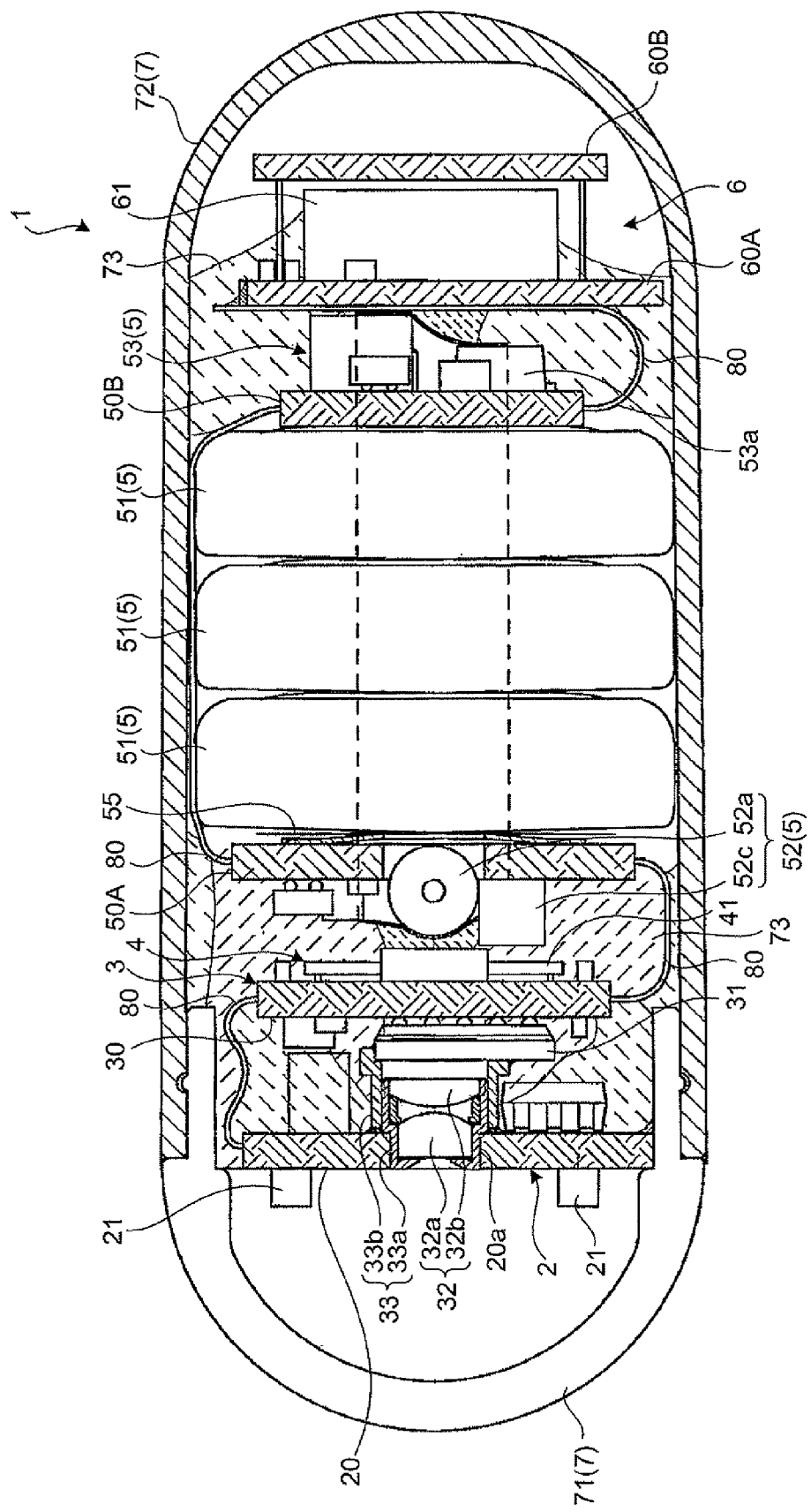
FIG. 15 is a cross-sectional side view showing a configuration of a capsule endoscope as being a capsule-type medical apparatus according to a second embodiment of the invention.

As shown in FIG. 15, the capsule endoscope 1 mainly includes the internal components, for predetermined functions, consisting of the illumination unit 2, the imaging unit 3, the drive unit 4, the transmission unit 6; and the sealed container 7 accommodating the internal components.

As shown in FIG. 15, the power supply unit 5 includes the battery 51, the switch unit 52, and the power supply unit 53. For example, the battery 51 consists of a button-shaped silver oxide battery whose outline is round. The plural button-shape silver oxide batteries (three batteries in the second embodiment) are serially arranged while the negative electrode side is orientated toward the rear side. The battery 51 may be not only the silver oxide battery but also a storage-type battery, a generating type battery, and the like.

Figure 16:
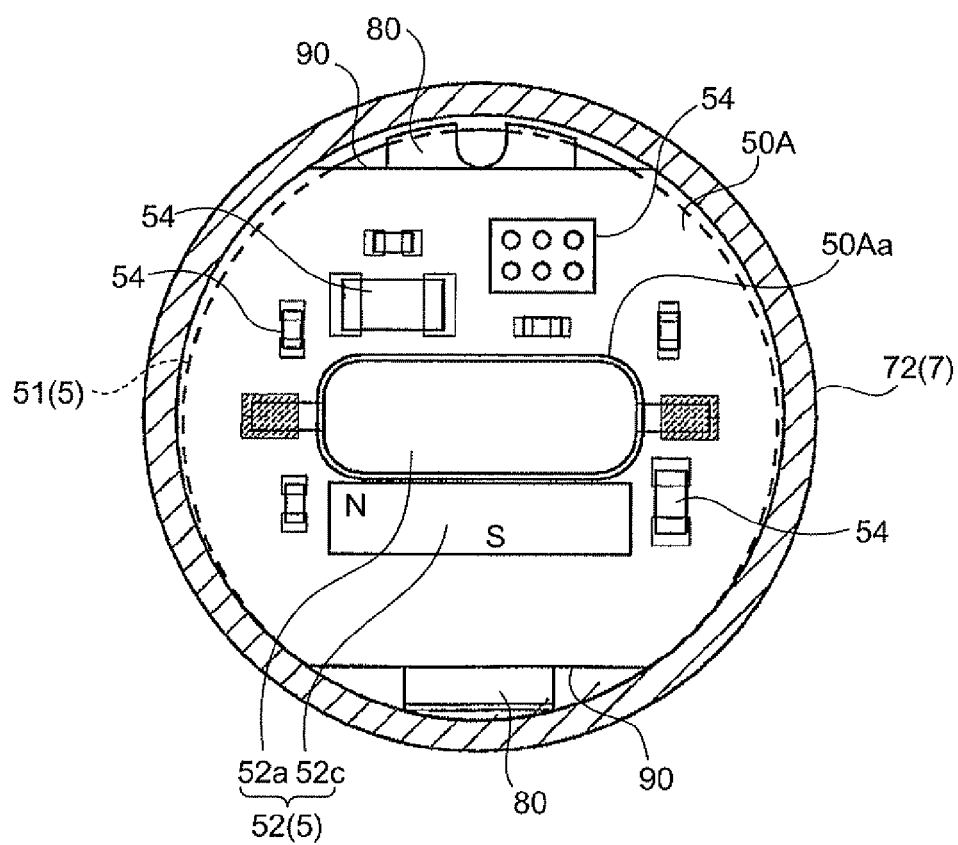
FIG. 16 is a cross-sectional view showing a switch board according to the second embodiment when viewed from the front surface.

As shown in FIG. 15, the switch unit 52 includes the reed switch 52a and a bias magnet 52c. As shown in FIG. 16, the reed switch 52a and the bias magnet 52c are provided in the front surface of the disk-shaped switch board 50A. As shown in FIG. 15, the reed switch 52a is inserted into the cutout hole 50Aa made in the switch board 50A, and the reed switch 52a is fixed by the adhesive agent, which suppresses the projection height of the reed switch 52a toward the front surface of the switch board 50A to achieve the downsizing of the switch unit 52. The reed switch 52a is a normally-OFF type switch, and the reed switch 52a always becomes the ON state by combination of the reed switch 52a and the bias magnet 52c. The ON state of the reed switch 52a turns on the main power supply of the capsule endoscope 1.

In the switch unit 52, the reed relay internally provided in the reed switch 52a is located in parallel with the lengthwise direction (direction between poles) of the bias magnet 52c. This enables the stable magnetic force of the bias magnet 52c which acts on the reed switch 52a to cause the reed switch 52a to always become the ON state. In the switch unit 52, the lengthwise direction (direction between magnetic poles) of the bias magnet 52c is parallel to the direction of the reed relay internally provided in the reed switch 52a. This enables the reed switch 52a to be stably operated. In the switch unit 52, the downsizing is achieved by adopting the normally-OFF type reed switch 52a.

As shown in FIG. 16, the chip components 54 are provided in the front surface of the switch board 50A. Examples of the chip component 54 include the memory and the oscillator. For example, the initial value of the DSP 41, the variations in color or white balance of the solid-state imaging device 31, and a specific number of the capsule endoscope 1 are stored in the memory. The oscillator supplied the basic clock to the DSP 41. As shown in FIG. 15, the contact 55 formed from a leaf spring is provided in the back surface of the switch board 50A. The contact 55 is in contact with the positive electrode of the battery 51.

The power supply unit 53 includes the DC-DC converter 53a. As shown in FIG. 8, the DC-DC converter 53a is provided on the back surface of the disk-shaped power supply board SOB. The DC-DC converter 53a controls the voltage supplied from the battery 51 in order to always obtain the constant voltage necessary for the system. A contact (not shown), which is in contact with the negative electrode of the battery 51, is provided in the front surface of the power supply board 50B. Thus, in the power supply unit 5, the battery 51 is serially placed between the switch board 50A and the power supply board 50B to supply the electric power.

In the configuration of the capsule endoscope 1, the lengthwise axis line of the internal component accommodated in the sealed container 7, i.e., orientation of rotating direction about the center axis becomes unknown, because the outline of the sealed container 7 is formed in the rotational symmetry shape with respect to the predetermined center axis. Therefore, the capsule endoscope 1 of the second embodiment includes orientation recognizing means for indication the accommodation direction about the center axis with respect to the sealed container 7 in the internal components accommodated in the sealed container 7. The orientation recognizing unit will be described below.

The orientation recognizing means is provided inside the sealed container 7 while being visible from the outside of the sealed container 7 through the front cover 71 which is of the transparent portion. In this case, an example of the orientation recognizing unit is provided in the illumination board 20 whose front-end side is covered with the front cover 71. As described above, the illumination board 20 is formed in the disc shape, the flexible board 80 which electrically connected the illumination board 20 and another board (imaging board 30) is integrated with the illumination board 20 while extended from the illumination board 20, and the flat portion 90 is provided in order to fold the extended portion of the flexible board 80. In the orientation recognizing unit, the flat portion 90 is set at an index. That is, the orientation of the flat portion 90 of the illumination board 20 is visible from the outside of the sealed container 7 through the front cover 71 which is of the transparent portion, and the orientation of the flat portion 90 indicates the accommodation direction in the internal components accommodated in the sealed container 7.

The direction of the taken image obtained by the imaging unit 3 is located in the accommodation direction of the internal component. As described above, the solid-state imaging device 31 of the imaging unit 3 images the range illuminated with the illumination light of the illumination unit 2 on the front surface side of the illumination board 20. The vertical direction is determined in the taken image. In the second embodiment, the flat portion 90 of the illumination board 20 is provided so that the vertical direction of the taken image becomes the proper orientation when the illumination board 20 is orientated upward as shown in FIG. 2. Therefore, in the case where the image is confirmed after the capsule endoscope 1 is assembled, the flat portion 90 which is made visible through the front cover 71 is orientated upward in the illumination board 20, which allows the orientation of the taken-image to coincide with the accommodation direction of the internal components.

Figure 17:
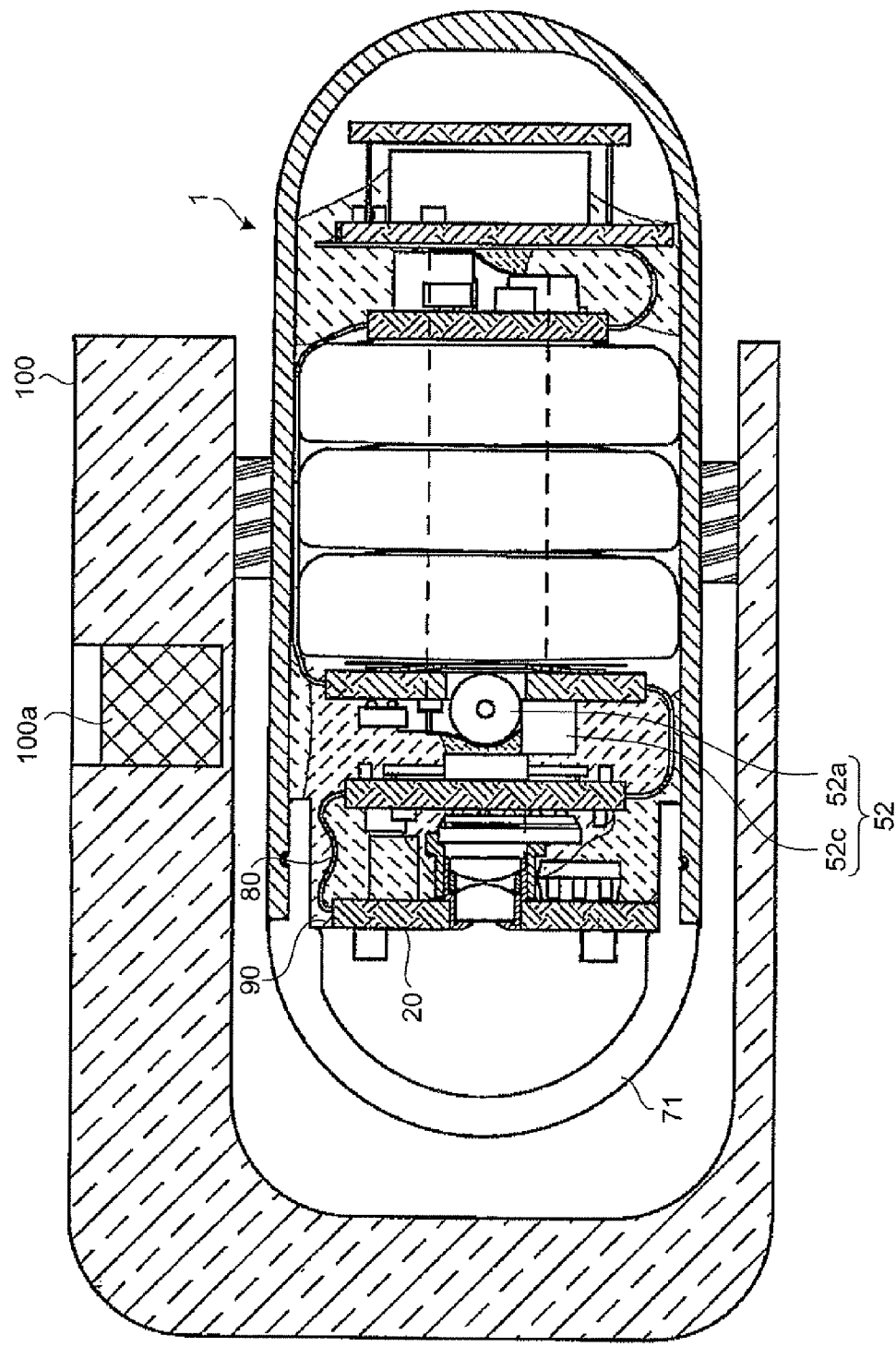
FIG. 17 is a longitudinal sectional view showing a state in which the capsule endoscope as being the capsule-type medical apparatus according to the second embodiment of the invention is accommodated in the package.
Figure 18:
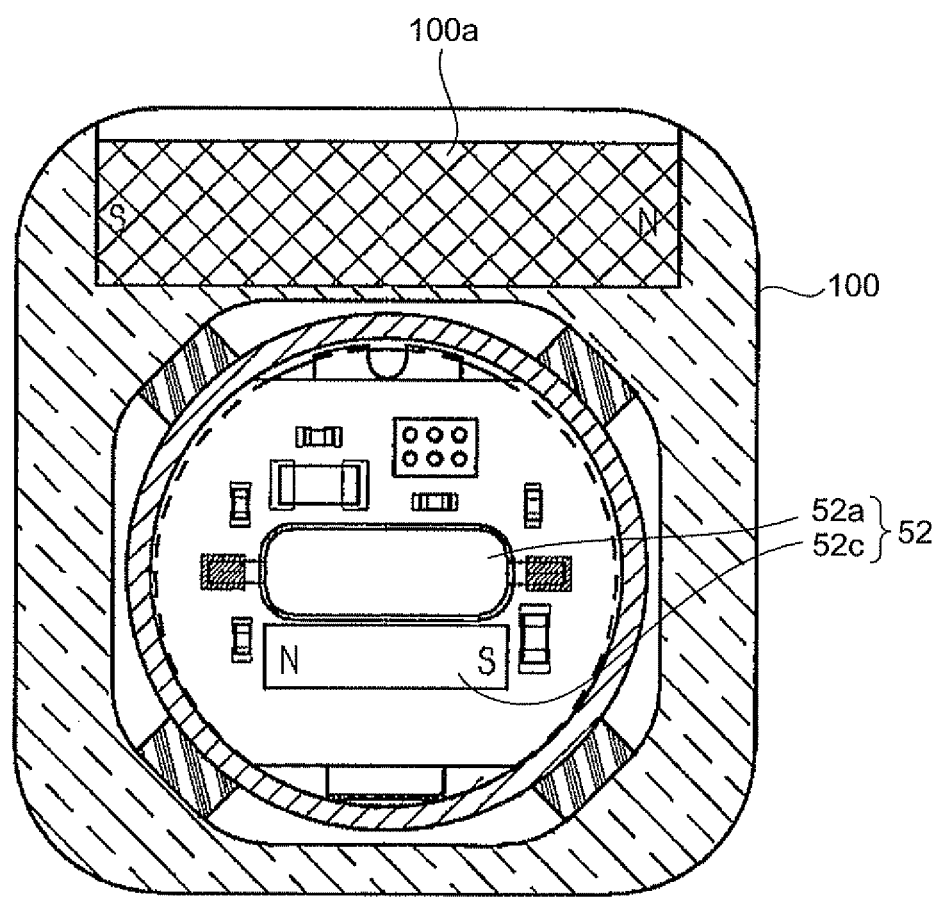
FIG. 18 is a transverse sectional view showing the state in which the capsule endoscope as being the capsule-type medical apparatus according to the second embodiment of the invention is accommodated in the package.

The direction of the reed switch 52a is also located in the accommodation direction of the internal component. The reed switch 52a of the second embodiment always becomes the ON state by the combination of the reed switch 52a and the bias magnet 52c. As shown in FIGS. 17 and 18, the assembled capsule endoscope 1 has the portability while stored in the package 100. The permanent magnet 100a is provided in the package 100. The magnetic field of the bias magnet 52c is disable when the permanent magnet 100a is orientated toward the reverse polarity of the bias magnet 52c of the switch unit 52. Therefore, the reed switch 52a of the switch unit 52 becomes the OFF state to turn off the main power supply of the capsule endoscope 1. That is, the direction of the reed switch 52a is located in the direction of the action magnetic field corresponding to the permanent magnet 100a, in order that the reed switch 52a becomes the OFF state when the capsule endoscope 1 is stored in the package 100. In the second embodiment, when the flat portion 90 of the illumination board 20 is provided such that the bias magnet 52c is orientated toward the reverse polarity of the permanent magnet 100a when the flat portion 90 is orientated upward. Therefore, in the case where the assembled capsule endoscope 1 is stored in the package 100, the flat portion 90, which is made visible through the front cover 71, is orientated upward in the illumination board 20, which allows the orientation of the reed switch 52a to coincide with the accommodation direction of the permanent magnet 100a.

As described above, in order to stabilize the operation of the reed switch 52a, the lengthwise direction (direction between magnetic poles) of the bias magnet 52c is parallel to the direction of the reed relay internally provided in the reed switch 52a. In addition, the lengthwise direction (direction between magnetic poles) of the permanent magnet 100a is parallel to the direction of the reed relay internally provided in the reed switch 52a. This enables the reed switch 52a to be stably operated.

The direction indicating the directivity of the antenna 62 is located in the accommodation direction of the internal component. In the second embodiment, there is no directivity because the antenna 62 is provided in the spiral pattern. However, it is also thought that the antenna 62 is configured to have the directivity in a predetermined direction. In this case, the flat portion 90 of the illumination board 20 is provided so that the antenna 62 has the preferable directivity (for example, upwardness) when the flat portion 90 is orientated upward as shown in FIG. 2. Therefore, in the case where the transmission and reception are confirmed after the capsule endoscope 1 is assembled, the flat portion 90, which is made visible through the front cover 71, is orientated upward in the illumination board 20, which allows the directivity of the antenna 62 to be secured.

In the second embodiment, the flat portion 90 provided in the illumination board 20, which is made visible through the front cover 72, is described as an example of the orientation recognizing unit. However, the invention is not limited to the flat portion 90. Alternatively, a shape except for the flat portion 90 indicating the orientation may be provided in the illumination board 20, or printing for indicating the orientation may be performed to the illumination board 20.

Instead of the orientation recognizing unit which is made visible from the outside through the front cover 72, for example, it is also possible that the direction can be indicated by the deviation of the center of gravity in a radial direction of the assembled capsule endoscope 1. In this case, for example, the center of gravity in the radial direction of the capsule endoscope 1 is shifted by a weight of the bias magnet 52c, and the capsule endoscope 1 is configured to be always orientated toward the same direction when the capsule endoscope 1 is placed on a flat portion. Alternatively, the battery 51 having the smaller diameter with respect to the radial direction of the sealed container 7 is adopted to shift the center of gravity in the radial direction of the capsule endoscope 1, and the capsule endoscope 1 is configured so that the orientation in the circumferential direction of the capsule endoscope 1 is always kept constant when the capsule endoscope 1 is placed on a flat portion. Thus, the orientation of the accommodated internal components can be indicated by the configuration in which the center of gravity in the radial direction of the capsule endoscope 1 is shifted.

As described above, the capsule endoscope 1 of the second embodiment includes the orientation recognizing unit for indicating the accommodation direction in the internal components accommodated in the sealed container 7. As a result, even if the outline of the sealed container 7 is molded in the rotational symmetry shape based on the axis line (central axis line) in the lengthwise direction by the substantially hemispherical front cover 71 and the cylindrical drum portion and substantially hemispherical rear-end portion of the cover 72, because the orientation in the rotating direction about the axis line in the lengthwise direction becomes clear, the accommodation direction of the internal component accommodated in the sealed container 7 can easily be recognized.

The orientation recognizing unit is provided inside the sealed container 7 while being visible from the outside of the sealed container 7 through the front cover 71 which is of the transparent portion constituting the sealed container 7, which allows the accommodation direction of the internal components accommodated in the sealed container 7 to be easily recognized without particularly changing the outline of the sealed container 7. Therefore, it is not necessary that a convex or a concave indicating the direction be provided in the outside of the sealed container 7.

The internal components have the illumination board 20 on which the emitter is provided. The emitter constitutes the illumination unit 2 in which the outside of the sealed container 7 is illuminated with the illumination light through the front cover 71 constituting the sealed container 7. The orientation recognizing unit is provided in the illumination board 20 while being visible from the outside of the sealed container 7 through the front cover 71. As a result, the orientation recognizing unit is provided in the necessary illumination board 20 incorporated into the capsule endoscope 1, so that the orientations of the internal components accommodated in the sealed container 7 can easily be recognized without increasing the number of internal components.

The illumination board 20 is formed in the disc shape, and the illumination board is integrally formed with the flexible board 80 which electrically connects the illumination board 20 and the other boards while extended. The flat portion 90 provided in the illumination board 20 in order to fold the extended portion of the flexible board 80 is used as the orientation recognizing unit. In the necessary illumination board 20 incorporated into the capsule endoscope 1, the flat portion 90 provided for another usage in the illumination means 20 is used as the orientation recognizing means, so that the orientations of the internal components accommodated in the sealed container 7 can easily be recognized without changing the internal components.

The orientation recognizing unit may be the deviation of the center of gravity in the state where the internal components are accommodated in the sealed container. As a result, even if the outline of the sealed container 7 is molded in the symmetrical shape based on the axis line in the lengthwise direction by the substantially hemispherical front cover 71 and the cylindrical drum portion and substantially hemispherical rear-end portion of the cover 72, because the orientation in the rotating direction about the axis line in the lengthwise direction becomes clear by the deviation of the center of gravity, the accommodation direction of the internal components accommodated in the sealed container 7 can easily be recognized.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule-type medical device, comprising:
a capsule-shape sealed container having a center axis, an outline of the sealed container being formed in a rotational symmetry shape with respect to the center axis, the sealed container being introduced into a subject while accommodating an internal component for executing a predetermined function, wherein
the internal component includes an illumination board in which an emitter constituting an illumination unit is provided,
the illumination unit emits an illumination light outside the sealed container through a transparent portion constituting at least a portion of the sealed container,
the illumination board has a disk shape that fits inside the sealed container formed in the rotational symmetry shape,
a flexible board that electrically connects between the illumination board and another board extends integrally with the illumination board,
the illumination board has a flat portion formed on a periphery of the disk-shaped illumination board so as to truncate the disk-shape, and the flat portion is provided to fold the flexible board extending from the disk-shaped illumination board at an end portion at an illumination board side of the flexible board,
the flat portion is visible from outside of the sealed container through the transparent portion, and
the flat portion indicates a direction corresponding to the predetermined function of the internal component.

2. The capsule-type medical device according to claim 1, wherein the illumination unit has a light-emitting diode.

3. A capsule-type medical apparatus comprising:
the capsule-type medical device according to claim 1 as a capsule main body.

4. The capsule-type medical apparatus according to claim 3, further comprising:
a package that accommodates the capsule main body,
wherein the internal component further includes a reed switch that becomes an ON state by a magnetic field from outside the capsule main body,
wherein the package includes an external magnet that generates the magnetic field from outside the capsule main body, and
wherein the capsule main body is accommodated in the package so that positions of the flat portion and the external magnet are fixed relative to each other.

5. The capsule-type medical apparatus according to claim 4, wherein the reed switch becomes the ON state by the magnetic field generated by the external magnet to turn off a power of the capsule main body when the capsule main body is accommodated in the package.

* * * * *

UNITED STATES PATENT AND TRADEMARK OFFICE
CERTIFICATE OF CORRECTION

| | |
|---|---|
| PATENT NO. | : 8,602,977 B2 |
| APPLICATION NO. | : 12/013883 |
| DATED | : December 10, 2013 |
| INVENTOR(S) | : Noriyuki Fujimori et al. |

Page 1 of 1

It is certified that error appears in the above-identified patent and that said Letters Patent is hereby corrected as shown below:

Title Page
Item (75) Inventors: should read:

-- (75) Inventors:  Noriyuki Fujimori, Nagano (JP);
Hiroshi Suzushima, Nagano (JP); --.

Signed and Sealed this
Twenty-ninth Day of April, 2014

Michelle K. Lee
*Deputy Director of the United States Patent and Trademark Office*